(12) United States Patent  
Yoon (10) Patent No.: US 11,921,129 B2
(45) Date of Patent: Mar. 5, 2024

(54) AUTOMATIC SPECIMEN FEEDING SYSTEM AND CONTROL METHOD THEREFOR

(71) Applicant: APM ENGINEERING CO., LTD., Bucheon-si (KR)

(72) Inventor: Gwan Hoon Yoon, Paju-si (KR)

(73) Assignee: APM ENGINEERING CO., LTD., Bucheon-si (KR)

( * ) Notice: Subject to any disclaimer, the term of this patent is extended or adjusted under 35 U.S.C. 154(b) by 393 days.

(21) Appl. No.: 17/418,710

(22) PCT Filed: Nov. 28, 2019

(86) PCT No.: PCT/KR2019/016628
§ 371 (c)(1),
(2) Date: Jun. 25, 2021

(87) PCT Pub. No.: WO2020/138740
PCT Pub. Date: Jul. 2, 2020

(65) Prior Publication Data
US 2022/0065887 A1    Mar. 3, 2022

(30) Foreign Application Priority Data
Dec. 28, 2018 (KR) .................. 10-2018-0172889

(51) Int. Cl.
*G01N 35/10*    (2006.01)
*G01N 1/00*    (2006.01)

(52) U.S. Cl.
CPC ... *G01N 35/1065* (2013.01); *G01N 2001/002* (2013.01); *G01N 2035/1048* (2013.01)

(58) Field of Classification Search
CPC ......... G01N 35/1065; G01N 2001/002; G01N 2035/1048
(Continued)

(56) References Cited

U.S. PATENT DOCUMENTS 11,092,519 B1 *    8/2021    Hilliard ............. G01N 35/0099

FOREIGN PATENT DOCUMENTS

JP    10-123122 A    5/1998
JP    10123122 A *    5/1998
(Continued)

OTHER PUBLICATIONS

Translation of JP-10123122-A (provided by Applicant) (Year: 1998).*

*Primary Examiner* — Nathaniel T Woodward
(74) *Attorney, Agent, or Firm* — Maschoff Brennan (57) ABSTRACT

Disclosed is an automatic specimen feeding system and a control method therefor. The automatic specimen feeding system includes a main frame installed adjacent to a carbon measuring apparatus, having a space with an open upper portion; a specimen seating unit which reciprocates horizontally in a direction perpendicular to the carbon measuring apparatus while moving up and down with respect to the main frame, and on which a plurality of specimens can be seated; a specimen lift unit which is installed under the specimen seating unit and can lift one of the plurality of specimens seated on the specimen seating unit; and a specimen input unit which is installed lengthways in the direction towards the carbon measuring apparatus to grip specimens lifted by the specimen lift unit and to input the specimens into the carbon measuring apparatus.

10 Claims, 4 Drawing Sheets

(58) Field of Classification Search
USPC .......................................................... 73/863
See application file for complete search history.

(56) References Cited

FOREIGN PATENT DOCUMENTS

| | | |
|---|---|---|
| JP | 2013-213709 A | 10/2013 |
| KR | 10-2010-0028615 A | 3/2010 |
| KR | 10-1674884 B1 | 11/2016 |
| KR | 10-2018-0020427 A | 2/2018 |

\* cited by examiner

AUTOMATIC SPECIMEN FEEDING SYSTEM AND CONTROL METHOD THEREFOR

TECHNICAL FIELD

The present invention relates to an automatic specimen feeding system and a control method therefor, and more particularly, to an automatic specimen feeding system and a control method therefor to automatically perform all processes of preparing and supplying a plurality of specimens for measuring carbon, performing a carbon measurement process and then discarding the used specimen.

BACKGROUND ART

The carbon component in particulate matter in the atmosphere is a very important component, and particle mass accounts for 10% to 40%. The particulate carbon component is produced in the form of impurities generated by incomplete combustion of fossil fuels and secondary photochemical reactions in the atmosphere, and serves as a major constituent, accounting for 10% to 40% of particles suspended in the urban atmosphere.

The particulate carbon components are mainly classified into organic carbon, elemental carbon and carbonate carbon, Studies have shown that the particulate carbon components may cause air pollution and affect global warming (Jacobson, 2001; Hansen et al., 2000).

There are apparatuses by a thermal-optical analysis scheme for a method of analyzing the carbon component in the particulate matter in the atmosphere, and one analysis time may take about 20 minutes. In general, when specimens are supplied by manpower the maximum number of specimens that can be analyzed per day is about 20, so only a small number of specimens may be analyzed. Thus, the amount of specimens to be analyzed is too small, and accordingly the efficiency is not preferable and only the cost increases.

DISCLOSURE

Technical Problem

Accordingly, the present invention is disclosed to solve the above problems. An object of the present invention is to provide an automatic specimen feeding system and a control method therefor so as to improve user convenience by supplying a large number of specimens to the carbon measuring apparatus, and simultaneously performing the process of discarding used specimens without using manpower.

In addition, another object of the present invention is to provide an automatic specimen feeding system and a control method therefor to significantly reduce the time required to feed specimens to a carbon measuring apparatus.

Technical Solution

The present invention to achieve the above problems includes: a main frame installed adjacent to a carbon measuring apparatus for measuring carbon, formed with a space having an opened upper portion, and having an input hole for inputting a specimen to the carbon measuring apparatus; a specimen seating unit horizontally reciprocating in a direction orthogonal to the carbon measuring apparatus while ascending and descending in the main frame, and seated thereon with a plurality of specimens; a specimen lift unit installed under the specimen seating unit to lift one of the specimens seated on the specimen seating unit; a specimen input unit installed lengthways toward the carbon measuring apparatus to hold the specimen lifted by the specimen lift unit and input the specimen to the carbon measuring apparatus.

In addition, the present invention may further include a blower unit provided on the main frame or the specimen input unit to blow the specimen used in the carbon measuring apparatus from the specimen input unit to the mainframe or to a waste space provided nearby.

In addition, the specimen lift unit may include: a lift member including a plate-shaped lift base, a plurality of finger protrusions protruding upward from both ends of both edges of the lift base, and locking protrusions horizontally protruding from upper portions of the finger protrusions, respectively, so as to protrude inwardly to the inside of the lift base to lift lower sides of both edges of the specimen; and an elevation driving portion connected to a bottom surface of the lift base to elevate the lift member.

In addition, the specimen input unit may include an auxiliary frame installed on the upper portion of the main frame, and having a box-shaped frame in which upper and lower portions are opened, a rotating member arranged lengthways toward the carbon measuring apparatus and rotatably installed on the auxiliary frame, a moving member rotatably coupled to the rotating member and reciprocating in a lengthwise direction of the rotating member along the rotating member when the rotating member is rotated, a specimen input member coupled to the moving member to move together with the moving member, and holding the specimen lifted by the specimen lift unit to input the specimen to the carbon measuring apparatus, and a driving unit for rotating the rotating member, wherein the auxiliary frame may be divided, by a partition wall, into an operation space for holding the specimen, an installation space for installing the specimen input member, the moving member, and the rotating member, and the partition wall may be formed therein with a through-hole through which an end of the specimen input member passes.

In addition, the specimen input member may include a bar-shaped member rotatably coupled to the moving member, and a spoon provided at an end of the bar-shaped member and passing through the through-hole to hold the specimen in the operation space.

In addition, the specimen input unit may further include a specimen input member rotating portion for rotating the specimen input member to drop the specimen placed on the spoon and completed in measuring carbon and dispose the dropped specimen to a waste space.

In addition, the specimen input member rotating port ion may include at least one protrusions protruding from an outer circumferential surface of an end of the specimen input member, a housing protruding from the auxiliary frame toward the installation space and opened at one side thereof, and a guide surface formed as a curved groove formed from the opening toward a bottom of the housing.

In addition, the specimen input unit may further include a blocking unit for blocking the through-hole while reciprocating in a width direction of the auxiliary frame in a condition in which the blocking unit is close to on e side of the partition wall on the operation space side.

In addition, the present invention may include: a preparation step of seating a plurality of specimens in a specimen seating unit and mounting and preparing the specimen seating unit on an installation frame movably installed on a main frame vertically and horizontally; a specimen lift step, after the preparation step, of lifting a specimen seated on the specimen seating unit to a position higher than an input hole of the main frame by operating a lift unit by operating an elevation driving portion of a specimen lift unit; a specimen holding step, after the specimen lift step, of holding the specimen lifted by the specimen lift unit by moving a specimen input member toward the input hole by operating a specimen input unit; a carbon measuring step, after the specimen holding step, of measuring carbon by driving a carbon measuring apparatus by introducing the specimen into the carbon measuring apparatus through the input hole by operating the specimen input unit; and a specimen removing step, after the carbon measuring step, of moving the specimen completed in measuring carbon toward the main frame, and then discarding the specimen from the specimen input unit to a waste space.

In addition, the specimen removing step may further include a blower step capable of blowing the specimen seated on the specimen input member into the waste space by using wind, by operating a specimen blower unit installed on the main frame or an auxiliary frame.

Advantageous Effects

According to the present invention, a large number of specimens are automatically processed to a carbon measuring apparatus without using manpower to measure carbon, so that user convenience can be improved.

In addition, the specimen of the specimen cassette is lifted by the specimen lift unit, seated on the spoon, immediately fed to the carbon measuring apparatus, so that the time required for the process of supplying and inspecting specimens can be significantly reduced.

In addition, the specimen is lifted from the specimen cassette as the lift unit ascends, and the specimen is seated on the spoon as the lift unit descends, so that the specimen can be prevented from dropping when the specimen is held or released.

BEST MODE

Mode for Invention

As a best mode, the present invention proposes an automatic specimen feeding system including: a main frame installed adjacent to a carbon measuring apparatus for measuring carbon, formed with a space having an opened upper portion, and having an input hole for inputting a specimen to the carbon measuring apparatus; a specimen seating unit horizontally reciprocating in a direction orthogonal to the carbon measuring apparatus while ascending and descending in the main frame, and seated thereon with a plurality of specimens; a specimen lift unit installed under the specimen seating unit to lift one of the specimens seated on the specimen seating unit; and a specimen input unit installed lengthways toward the carbon measuring apparatus to hold the specimen lifted by the specimen lift unit and input the specimen to the carbon measuring apparatus.

In addition, as a best mode, the present invention proposes a control method of the automatic specimen feeding system, which includes: a preparation step of seating a plurality of specimens in a specimen seating unit, and mounting and preparing the specimen seating unit on an installation frame movably installed on a main frame vertically and horizontally; a specimen lift step, after the preparation step, of lifting a specimen seated on the specimen seating unit to a position higher than an input hole of the main frame by operating a lift unit by operating an elevation driving portion of a specimen lift unit; a specimen holding step, after the specimen lift step, of holding the specimen lifted by the specimen lift unit by moving a specimen input member toward the input hole by operating a specimen input unit; a carbon measuring step, after the specimen holding step, of measuring carbon by driving a carbon measuring apparatus, by introducing the specimen into the carbon measuring apparatus through the input hole by operating the specimen input unit; and a specimen removing step, after the carbon measuring step, of moving the specimen completed in measuring carbon toward the main frame, and then discarding the specimen from the specimen input unit to a waste space.

Best Mode for Embodiment of the Present Invention

The terms and words used in the specification and claims of the present invention will not be construed as limited to the conventional or lexical meaning, and will be construed as the meanings and concepts based on the principle that "an inventor may define the concept of the term properly in order to describe the invention in the best way".

In addition, the embodiments described in the present specification and the configurations shown in the drawings are merely exemplary embodiments according to the present invention, and may not represent all of the technical ideas of the present invention. Therefore, it will be understood that various equivalents and modifications may be substituted therefor at the time of filing of the present application.

Figure 1:
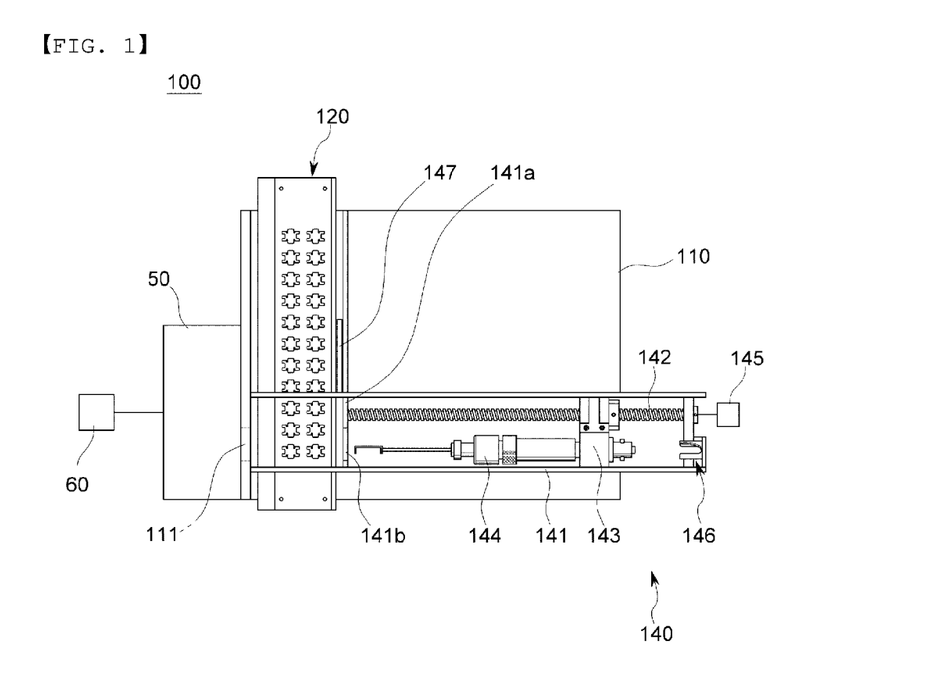
FIG. 1 is a plan view showing an automatic specimen feeding system according to the first embodiment of the present invention.
Figure 2:
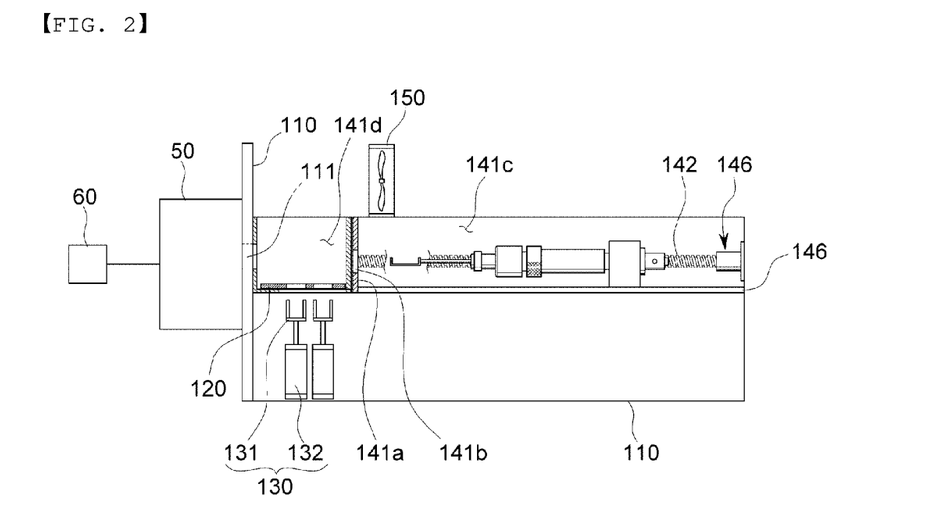
FIG. 2 is a lateral sectional view showing the automatic specimen feeding system according to the first embodiment of the present invention.
Figure 3:
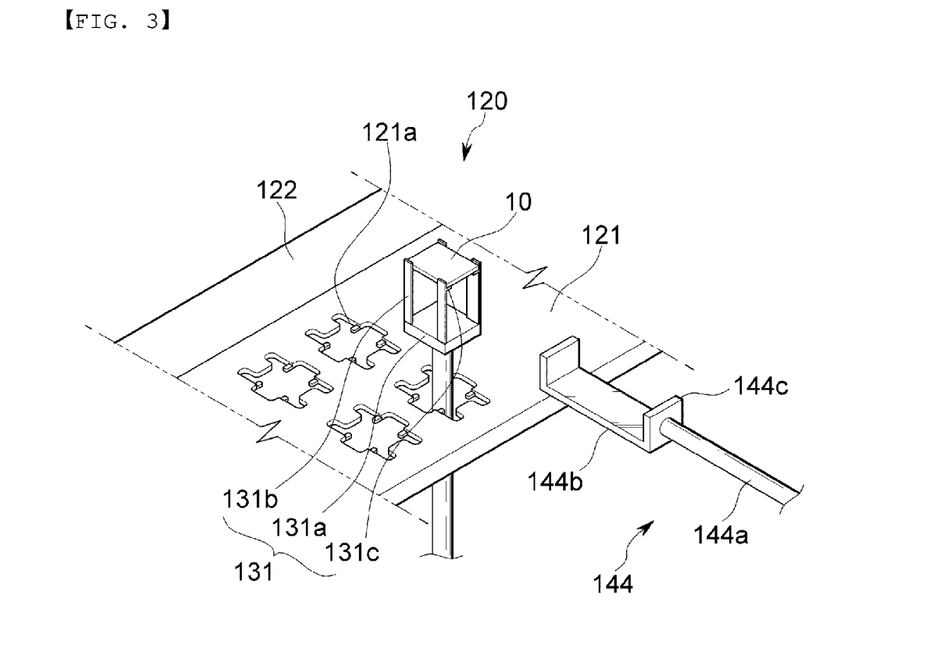
FIG. 3 is a perspective view showing a state in which a specimen is lifted from a specimen seating unit by using a specimen lift unit in the automatic specimen feeding system of FIG. 1.
Figure 4:
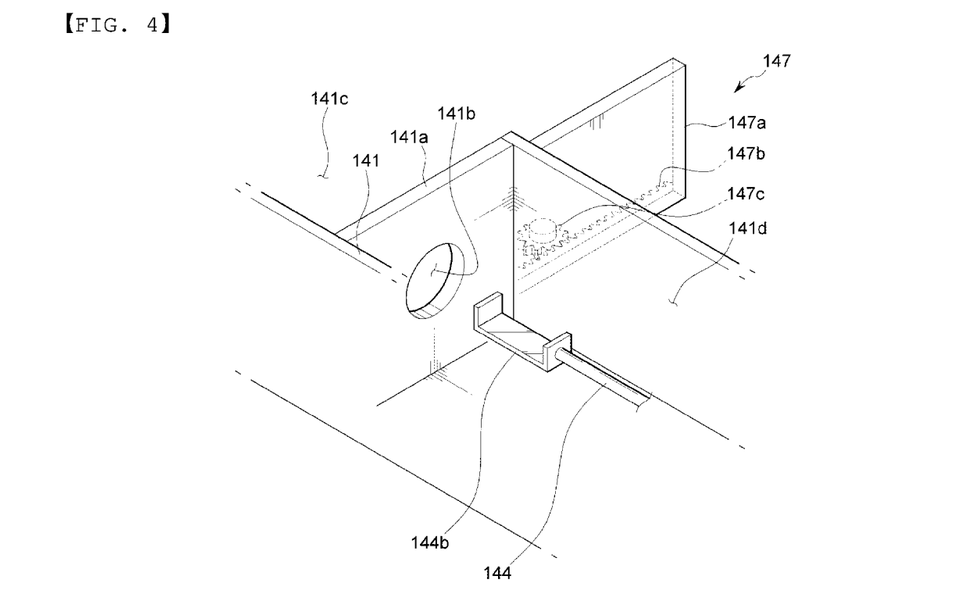
FIG. 4 is a perspective view of a main part showing a structure of a through-hole of an auxiliary frame and a blocking unit in the automatic specimen feeding system of FIG. 1.
Figure 5:
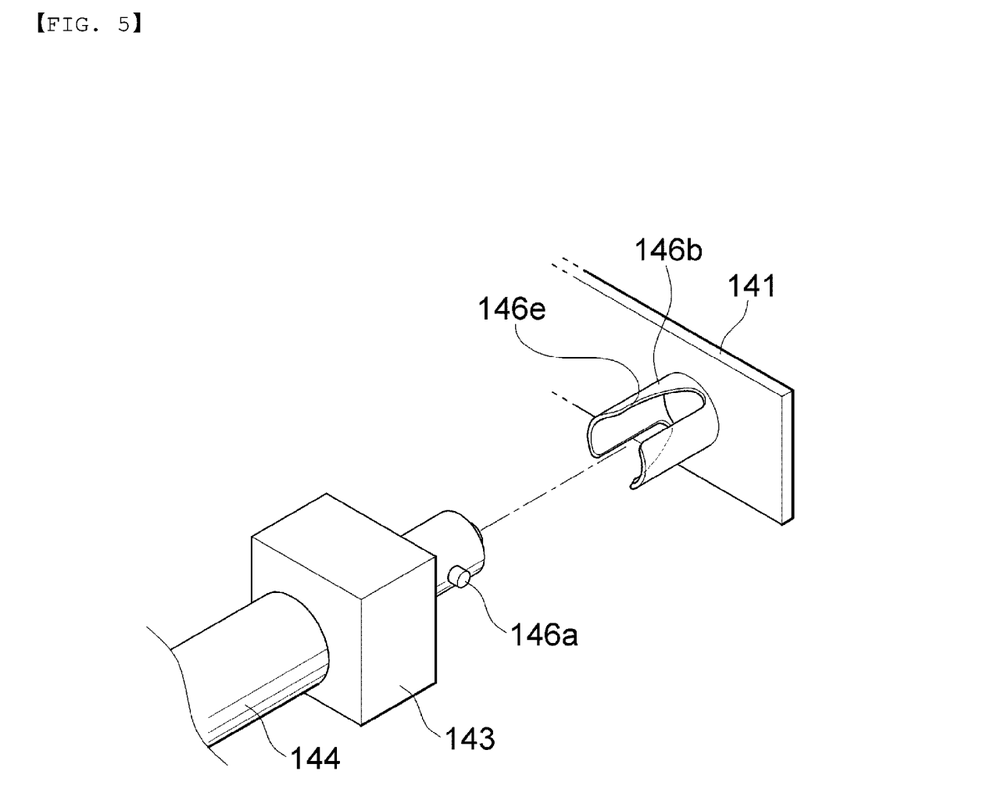
FIG. 5 is a perspective view showing a rotating portion of a specimen input member in the automatic specimen feeding system of FIG. 1.

FIG. 1 is a plan view showing an automatic specimen feeding system according to the first embodiment of the present invention. FIG. 2 is a lateral sectional view showing the automatic specimen feeding system according to the first embodiment of the present invention. FIG. 3 is a perspective view showing a state in which a specimen is lifted from a specimen seating unit by using a specimen lift unit in the automatic specimen feeding system of FIG. 1. FIG. 4 is a perspective view of a main part showing a structure of a through-hole of an auxiliary frame and a blocking unit in the automatic specimen feeding system of FIG. 1. FIG. 5 is a perspective view showing a rotating portion of a specimen input member in the automatic specimen feeding system of FIG. 1.

Referring to FIGS. 1 to 5, an automatic specimen feeding system 100 is configured to supply a specimen to a carbon measuring apparatus 50 for measuring carbon, and may include a main frame 110, a specimen seating unit 120, a specimen lift unit 130, a specimen input unit 140, and a specimen blower unit 150.

First, the main frame 110 may be formed in the shape of a box (cuboid) having a space portion in which an upper part is opened. In the main frame 110 with reference to FIG. 1, it is assumed that the direction to the left and right is referred to as being arranged in a length direction and the direction to the front and rear is referred to as a width direction in drawings.

A carbon measuring apparatus 50 capable of measuring carbon may be installed in the vicinity of the main frame 110. In other words, as shown in FIG. 1, the carbon measuring apparatus 50 may be installed adjacent to one side (left side) of the main frame 110. An input hole 111, through which a specimen 10 may be introduced into the carbon measuring apparatus 50, may be formed on one surface (left surface in the drawing) of the main frame 110 adjacent to the carbon measuring apparatus 50.

The specimen seating unit 120 is configured to mount a plurality of specimens 10 and arrange the specimens to a position of the input hole 111 of the main frame 110 to measure carbon, and may include a specimen cassette 121, a horizontal moving unit, a lifting unit, and a position detecting unit.

The specimen cassette 121 may be configured to be installed close to the one surface of the main frame 110 in which the input hole 111 is formed, so as to reciprocate in the width direction of the main frame 110. When being longer than the length in the width direction of the main frame 110, the specimen cassette 121 may be configured to reciprocate in the width direction of the main frame 110 while being installed to pass through side surfaces of the main frame 110 in the width direction.

The specimen cassette 121 may be detachably installed to a separate installation frame 122 that moves up and down while reciprocating in the width direction of the main frame 110. In the specimen cassette 121, it is assumed that a portion arranged in the horizontal moving direction, that is, in the width direction of the main frame 110, is referred to as a length direction, and the length direction of the main frame 110 is referred to as a width direction. The specimen cassette 121 may be formed of a plate member having a predetermined length and width, and provided with a plurality of seating portions 121a in which a plurality of specimens 10 may be seated. The seating portion 121a may include a through-hole vertically formed through the specimen cassette 121, and a plurality of locking protrusions protruding from an inner edge of the through-hole.

A plurality of seating portions 121a may be formed in the lengthwise direction of the specimen cassette 121, so as to be spaced apart from each other by a predetermined interval. The seating portions 121a formed in the lengthwise direction of the specimen cassette 121 as described above may be formed with one or more rows in the width direction of the specimen cassette 121.

The horizontal moving unit may be configured as a cylinder to reciprocate the separate installation frame 122, to which the specimen cassette 121 is mounted, in the front-rear direction of the main frame 110. In other words, the horizontal moving unit may be configured as a cylinder connected to the bottom or one side of the installation frame 122. The horizontal moving unit may also be configured to include a rack gear provided on one side of the installation frame 122, a pinion gear engaged to the rack gear, and a motor that generates rotational force to rotate the pinion gear.

The lift unit may be configured as a cylinder to elevate (vertically move) the installation frame 122 to which the specimen cassette 121 is detachable.

The position detecting unit may be provided with a first sensor at one end or the other end of the specimen cassette 121 to set an initial position of the specimen cassette 121. In addition, the specimen cassette 121 may be provided with position sensors at positions corresponding to the seating portions 121a, so that each of the seating portions 121a is positioned at the position of the input hole 111 through which the specimen 10 is inputted into the carbon measuring apparatus 50.

The specimen lift unit 130 is configured to lift the specimen 10 seated on the seating portion 121a of the specimen cassette 121 up to the position of the input hole 111 through which the specimen 10 may be inputted into the carbon measuring apparatus 50, and may include a lift member 131 and an elevation driving portion 132.

The lift member 131 may include a lift base 131a connected to the elevation driving portion 132 to be described later, a plurality of finger protrusions 131b protruding upward from both ends of both edges of the lift base 131a, and locking protrusions 131c protruding from upper ends of the finger protrusions 131b inwardly to the lift base 131a.

Although having been illustrated as being provided in two pairs in the drawings as an example, the finger protrusions 131b may be configured in two or more pairs. A distance between the pair of finger protrusions 131b facing each other among the finger protrusions 131b may be greater than a width of the specimen 10.

The elevation driving portion 132 may be configured as a cylinder connected to a bottom surface of the lift member 131 to move the lift member 131 up and down.

The specimen input unit 140 may be installed on an upper portion of the main frame 110 so as to be installed in both directions of the main frame 110, that is, in the direction toward the carbon measuring apparatus 50, so that the specimen may be inputted into the carbon measuring apparatus 50.

The specimen input unit 140 may include an auxiliary frame 141 formed at the upper portion of the main frame 110 to have a box-shaped frame in which upper and lower portions are opened, a rotating member 142 rotatably installed to the auxiliary frame 141, a moving member 143 reciprocating along the rotating member 142 when the rotating member 142 is rotated, a specimen input member 144 coupled to the moving member 143 to input the specimen to the carbon measuring apparatus 50 while moving together with the moving member 143, and a driving portion 145 for generating motive power.

The auxiliary frame 141 may be formed of a box-shaped frame member, and may be installed to be long in the lengthwise direction of the main frame 110. The auxiliary frame 141 may be formed with a partition wall 141a in a middle thereof so as to be divided into an operation space 141d and an installation space 141c. The partition wall 141a is formed therein with a through-hole 141b through which the specimen input member 144 may reciprocate, such that the specimen input member 144 may move from the installation space 141c toward the operation space 141d described later.

The operation space 141d refers to a space in which the carbon measuring apparatus 50 may perform an operation capable of holding the specimen 10 seated in the specimen cassette 121 to measure carbon.

The installation space 141c refers to a space for installing a specimen input member 144, which holds the specimen to input the specimen 10 to the carbon measuring apparatus, the rotating member 142, and the moving member 143.

The rotating member 142 is rotatably coupled between one side of the auxiliary frame 141 and the partition wall 141a, and may be rotated by driving of the driving portion 145. The rotating member 142 may be configured as a screw member formed on an outer circumferential surface thereof with a thread. In other words, the screw member serving as the rotating member 142 may have both ends coupled to the one side of the auxiliary frame 141 and the partition wall 141a so as to be idle. In other words, the rotating member 142 may be arranged in the lengthwise direction of the auxiliary frame 141.

The moving member 143 may be screwed to the rotating member 142 to reciprocate along the rotating member 142 in the lengthwise direction of the main frame 110 when the rotating member 142 is rotated.

The specimen input member 144 may be coupled to the moving member 143 to reciprocate in the lengthwise direction of the main frame 110 together with the moving member 143 when the moving member 143 is moved.

The specimen input member 144 may include a bar-shaped member 144a having a predetermined length and arranged toward the partition wall 141a in parallel with the rotating member 142 when coupled to the moving member 143, and a spoon 144b provided at an end of the bar-shaped member 144a and placed thereon with the specimen 10. The spoon 144b may have a side section formed in a significantly rectangular 'C' shape to have locking pieces 144c bent upward in which a front end and a rear end of a plate member having a predetermined length. In other words, the specimen 10 is placed on an upper surface of the spoon 144b, and then caught by the front and rear locking pieces 144c, so that the specimen 10 may be prevented from being separated from the upper surface of the spoon 144b when the specimen input member 144 reciprocates forward and backward (in the lengthwise direction of the main frame).

The specimen input unit 144 may further include a specimen input member rotating portion 146 for rotating the specimen input member 144, so that a specimen 10 placed on the spoon 144b may be dropped and thrown away after completion of the measurement for carbon of the specimen 10 placed on the spoon 144b.

The specimen input member rotating portion 146 may include at least one protrusions 146a protruding from an outer circumferential surface of an end of the specimen input member 144, a housing 146b protruding from one side surface of the auxiliary frame 141 toward the installation space 141c, having a cylindrical shape, and opened at one side thereof, and a guide surface 146c formed as a curved groove formed from the opening of the housing 146b toward a bottom of the housing 146b.

The specimen blower unit 150 may be coupled to the upper portion of the auxiliary frame 141 so as to be installed adjacent to the partition wall 141a in the upper portion of the installation space 141c, thereby allowing the specimen 10, which is mounted on the spoon 144b and completed in the carbon measurement, to be blown and moved a waste space (not shown) provided in the main frame 110 or provided outside.

The specimen blower unit 150 may include a blower fan for generating wind to blow the specimen 10 toward the waste space of the main frame 110.

The control unit 60 may be connected to each of the carbon measuring apparatus 50 and the automatic specimen feeding system 100 to control operations thereof.

More specifically, the control unit 60 may be connected to the specimen seating unit 120, the specimen lift unit 130, the specimen input unit 140, and the specimen blower unit 150 in the automatic specimen feeding system 100, and may be in a programmed state on driving, operating sequence, driving information, and the like.

Meanwhile, the auxiliary frame 141 may further include a blocking unit 147 for blocking the through-hole 141b formed in the partition wall 141a while reciprocating in the width direction of the auxiliary frame 141, in a state close to one surface of the partition wall 141a, that is, the one surface of the partition wall 141a of the operation space 141d side. The blocking unit 147 serves to block the through-hole 141b to prevent the wind generated by the specimen blower unit 150 for blowing the specimen 10 toward the waste space from entering the operation space 141d.

The blocking unit 147 may include a blocking member 147a for blocking the through-hole 141b while sliding in a close contact with one surface of the partition wall 141a, a rack gear 147b provided at a lower portion of the blocking member 147a, a pinion gear 147c gear-engaged and rotated with the rack gear 147b, and a drive motor that rotates the pinion gear 147c.

The blocking unit 147 is configured to be operated by the control unit 60, and may be operated to block the through-hole 141b of the partition wall 141a when the spoon 144b of the specimen input unit 144 exits the through-hole. In other words, a detection sensor (not shown) for detecting that the spoon 144b passes through the through-hole 141b may be provided around the through-hole 141b to transmit a signal to the control unit 60 when the spoon 144b inserted into the through-hole 141b and positioned in the carbon measuring apparatus 50 and the operation space 141d leaves the through-hole 141b and moves to the installation space.

Figure 6:
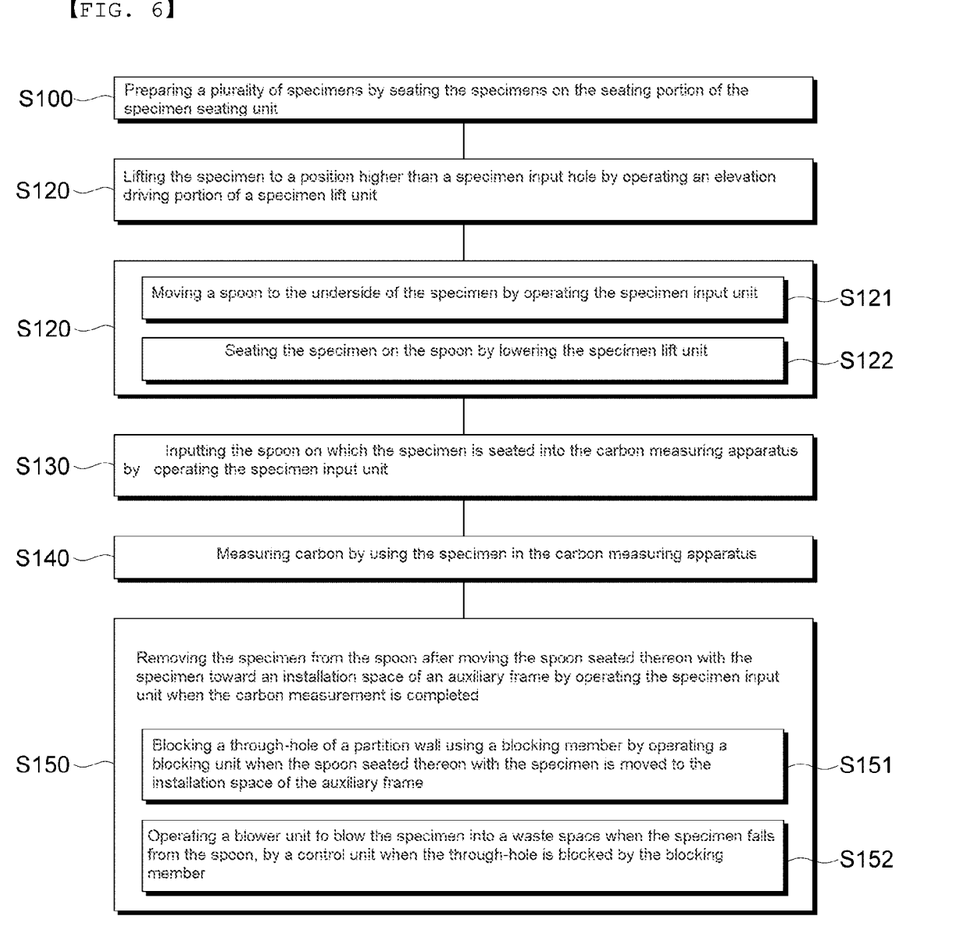
FIG. 6 is a view showing a control method of the automatic specimen feeding system according to the first embodiment of the present invention.

FIG. 6 is a view showing a control method of the automatic specimen feeding system according to one embodiment of the present invention.

First, referring to FIGS. 1 to 6, the operation method of the automatic specimen feeding system according to the embodiments of the present invention has a preparation step S100 of seating a plurality of specimens 10 on the specimen seating unit 120 to measure carbon.

In the preparation step S100, after all the specimens 10 may be seated in the seating portions 121a provided in the specimen cassette 121 of the specimen seating unit 120, the specimen cassette 121 may be mounted on the installation frame 122. In the preparation step S100, a user may operate the control unit 60 to set a mounting position of the specimen seating unit 120.

In other words, at the same time of setting the initial operating position of the specimen seating unit 120 by operating the control unit 60, operation sequences for each unit, such as an operation sequence of the specimen lift unit 130, an operation sequence of the specimen input unit 140, an operation of the carbon measuring apparatus 50, and an operation of the specimen blower unit 150, may also be required to be set in the control unit 60.

After the preparation step S100, the control unit 60 has a specimen lift step S110 of positioning the specimen at a position higher than the input hole 111 by lifting the specimen 10 in the seating part 121a of the specimen cassette 121 to a predetermined height by lifting the lift member 131 by operating the elevation driving portion 132 of the specimen lift unit 130.

After the specimen lift step S110, the control unit has a specimen holding step S120 of holding the specimen using the spoon 144b of the specimen input member 144 by moving the specimen input member 144 toward the operation space 141d by operating the driving portion 145 of the specimen input unit 140.

The specimen holding step S120 may include a first step S121 of straightly moving the spoon 144b in the installation space 141c to a lower side of the specimen 10 by operating the driving portion 145 of the specimen input unit 144, and a second step S122 of placing the specimen 10 on the spoon 144b while lowering the specimen lift member 131 by operating the specimen lift unit 130. When the spoon 144b is placed on the lower side of the specimen 10 in the first step S121, the specimen 10 is required to be positioned between the locking pieces 144c of the spoon 144b.

After the specimen holding step S120, the control unit 60 has a specimen input step S130 of inputting the specimen input member 144 into the carbon measuring apparatus 50 through the input hole 111 of the main frame 110 by operating the driving portion 145 of the specimen input unit 140.

After the specimen input step S130, the control unit 60 has a carbon measuring step S140 of measuring carbon through the specimen by operating the carbon measuring apparatus Thereafter, the control unit 60 has a specimen removing step S150 of moving the spoon of the specimen input member 144 toward the installation space 141c of the auxiliary frame 141 by operating the driving portion 145 of the specimen input unit 140, and then discarding the specimen 10 completed in the carbon measurement toward the main frame 110 or toward a waste space (trash bin) provided in the vicinity of the main frame 110.

In the specimen removing step S150, the specimen input member 144 may be rotated to drop and discard the specimen 10 seated on the spoon 144b into the waste space.

The specimen removing step S150, may further include a blower step S151 in which the control unit 60 operates the blower unit 150 when the specimen input member 144 is rotated, so as to blow the specimen 10 into the waste space when the specimen 10 drops from the spoon 144b.

The specimen removing step S150 may further include a blocking step S152 of blocking the through-hole 141b of the partition wall 141a using the blocking member 147a by operating the blocking unit 147, before the blower step S151 and after the spoon 144b of the specimen input member 144 passes through the through-hole 141b of the auxiliary frame 141 and moves to the installation space 141c.

The blocking step S is configured to block the through-hole 141b by using the blocking member 147, so that the wind generated by the blower unit 150 is prevented from entering the operation space 141d. In the control method of the automatic specimen feeding system according to the first embodiment of the present invention as described above, the above steps may be repeated until the measurement of carbon from the specimens 10 seated in the specimen seating unit 120 is completed.

Accordingly, since the specimen 10 seated in the specimen cassette 121 is lifted by the specimen lift unit 130, and then seated on the spoon 144b may be directly supplied to the carbon measuring apparatus 50, the time required for the process of supplying and inspecting specimens 10 can be significantly reduced.

The invention claimed is:

1. An automatic specimen feeding system comprising:
   a main frame installed adjacent to a carbon measuring apparatus for measuring carbon, formed with a space having an opened upper portion, and having an input hole for inputting a specimen to the carbon measuring apparatus;
   a specimen seating unit configured for horizontally reciprocating in a direction orthogonal to the carbon measuring apparatus while moving up and down in the main frame, and seated thereon with a plurality of specimens;
   a specimen lift unit installed under the specimen seating unit to lift one of the specimens seated on the specimen seating unit; and
   a specimen input unit installed lengthwise toward the carbon measuring apparatus to hold and input the specimen lifted by the specimen lift unit to the carbon measuring apparatus.

2. The automatic specimen feeding system of claim 1, further comprising:
   a blower unit provided on the main frame or the specimen input unit to blow the specimen used in the carbon measuring apparatus from the specimen input unit to the main frame or to a waste space provided nearby.

3. The automatic specimen feeding system of claim 1, wherein the specimen lift unit includes:
   a lift member including a plate-shaped lift base, a plurality of finger protrusions protruding upward from opposite ends of both edges of the lift base, and blocking protrusions horizontally protruding from upper portions of the finger protrusions so as to protrude inwardly to the lift base to lift lower sides of sides of the specimen, respectively; and
   an elevation driving portion connected to a bottom surface of the lift base to move the lift member up and down.

4. The automatic specimen feeding system of claim 1, wherein the specimen input unit includes:
   an auxiliary frame installed on the upper portion of the main frame, and having a box-shaped frame in which upper and lower portions are opened;
   a rotating member arranged long in the direction disposed with the carbon measuring apparatus and rotatably installed on the auxiliary frame;
   a moving member rotatably coupled to the rotating member and reciprocating in a lengthwise direction of the rotating member along the rotating member when the rotating member is rotated;
   a specimen input member coupled to the moving member to move together with the moving member, and gripping the specimen lifted by the specimen lift unit to input the specimen to the carbon measuring apparatus; and
   a driving unit for rotating the rotating member, and wherein
      the auxiliary frame is divided by a partition wall into an operation space for gripping the specimen, and an installation space for installing the specimen input member, the moving member, and the rotating member, and the partition wall is formed therein with a through-hole through which an end of the specimen input member passes.

5. The automatic specimen feeding system of claim 4, wherein the specimen input member includes:
   a bar-shaped member rotatably coupled to the moving member; and
   a spoon provided at an end of the bar-shaped member and passing through the through-hole to grip the specimen in the operation space.

6. The automatic specimen feeding system of claim 4, wherein the specimen input unit further includes:
- a sample input member rotating portion for rotating the specimen input member to drop and dispose the specimen, which is placed on the spoon and completed in measuring carbon, to a waste space.

7. The automatic specimen feeding system of claim 6, wherein the specimen input member rotating portion includes:
- at least one protrusions protruding from an outer circumferential surface of an end of the specimen input member;
- a housing protruding from the auxiliary frame toward the installation space and opened at one side thereof; and
- a guide surface formed as a curved groove formed from the opening toward a bottom of the housing.

8. The automatic specimen feeding system of claim 4, wherein the specimen input unit further includes:
- a blocking unit for blocking the through-hole while reciprocating in a width direction of the auxiliary frame in a condition in which the blocking unit is close to one side of the partition wall on the operation space side.

9. A method of controlling an automatic specimen feeding system, the method comprising:
- a preparation step of seating a plurality of specimens in a specimen seating unit, and mounting and preparing the specimen seating unit on an installation frame movably installed on a main frame vertically and horizontally;
- a specimen lift step, after the preparation step, of lifting a specimen seated on the sample seating unit to a position higher than an input hole of the main frame by operating a lift unit by operating an elevation driving portion of a specimen lift unit;
- a specimen gripping step, after the specimen lift step, of gripping the specimen lifted by the specimen lift unit by moving a specimen input member toward the input hole by operating a specimen input unit;
- a carbon measuring step, after the sample gripping step, of measuring carbon by driving a carbon measuring apparatus by introducing the specimen into the carbon measuring apparatus through the input hole by operating the specimen input unit; and
- a specimen removing step, after the carbon measuring step, of moving the specimen completed in measuring carbon toward the main frame, and then discarding the specimen from the specimen input unit to a waste space.

10. The method of claim 9, wherein the specimen removing step includes a blower step in which a specimen blower unit installed on the main frame or an auxiliary frame is operated to blow the specimen seated on the specimen input member into the waste space by using wind.

* * * * *